United States Patent [19]

Hagen et al.

[11] 4,267,349

[45] May 12, 1981

[54] PROCESS FOR THE PREPARATION OF 2-SUBSTITUTED-ALKYL-1-ALKYL-NITROIMIDAZOLES

[75] Inventors: Helmut Hagen, Frankenthal; Rolf-Dieter Kohler, Mannheim, both of Fed. Rep. of Germany

[73] Assignee: BASF Aktiengesellschaft, Fed. Rep. of Germany

[21] Appl. No.: 119,926

[22] Filed: Feb. 8, 1980

Related U.S. Application Data

[62] Division of Ser. No. 38,175, May 11, 1979.

[30] Foreign Application Priority Data

Jun. 22, 1978 [DE] Fed. Rep. of Germany ....... 2827351

[51] Int. Cl.$^3$ .................. C07D 233/94; C07D 233/93
[52] U.S. Cl. ..................................... 548/339; 548/338
[58] Field of Search ......................................... 548/339

[56] References Cited

PUBLICATIONS

Albright, J., et al., *J. Het. Chem.*, 10, 899–907 (1973).
Theilheimer, W., *Synthetic Methods of Organic Chemistry*, Interscience, New York, vol. 6 (1952), p. 214; vol. 12 (1958), p. 138; vol. 17 (1963), p. 94; vol. 24 (1970), p. 386.
Simchen, G., et al., *Liebigs Ann. Chem.* 1974, p. 1807 (No. 11).
*Chemical Abstracts*, 79:115436v (1973) [German OLS No. 2,203,542, 8/16/73, Hrstka et al.].
March, J., *Advanced Organic Chemistry*, McGraw-Hill, New York, 1968, pp. 458–459.
Wideqvist, S., *J. Am. Chem. Soc.*, 71, 4152 (1949).

*Primary Examiner*—Richard A. Schwartz
*Attorney, Agent, or Firm*—Keil & Witherspoon

[57] ABSTRACT

Novel 2-substituted 1-alkyl-nitroimidazoles and a process for their preparation by reaction of 2-methyl-nitroimidazoles with oxalic acid diesters, followed by reaction of the resulting nitroimidazol-2-yl-pyruvic acid esters with chlorine, in turn followed, if desired, by reaction of the resulting 2-dihalomethyl-nitroimidazoles with water.

Both the novel and the known compounds obtainable by the process of the invention are valuable starting materials for the preparation of dyes, pesticides and drugs.

16 Claims, No Drawings

PROCESS FOR THE PREPARATION OF 2-SUBSTITUTED-ALKYL-1-ALKYL-NITROIMIDAZOLES

This is a division, of application Ser. No. 38,175, filed May 11, 1979.

The invention relates to novel 2-substituted 1-alkyl-nitroimidazoles and a process for their preparation by reaction of 2-methyl-nitroimidazoles with oxalic acid diesters, followed by reaction of the resulting nitroimidazol-2-yl-pyruvic acid esters with chlorine, in turn followed, if desired, by reaction of the resulting 2-dihalomethylnitroimidazoles with water.

Liebigs Ann. Chem., (1975), 1,465–1,477 discloses that 2-formyl-1-methyl-5-nitroimidazole can be prepared by oxidizing 2-hydroxymethyl-1-methyl-5-nitroimidazole with manganese dioxide (loc. cit., 1,466):

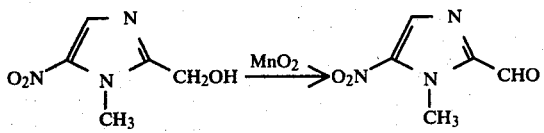

The transfer of this process to an industrial scale encounters substantial difficulties. A large excess of manganese dioxide is required. Disadvantages of the process are blockage of the filter, absorption of reaction mixture on the material filtered off, and hence the need to use large amounts of solvent. The yield of aldehyde depends greatly on the activity of the manganese dioxide employed; the latter must therefore always be freshly prepared. Both 2-hydroxymethyl-1-methyl-5-nitroimidazole and manganese dioxide are expensive starting materials.

It is also possible (J. Heterocycl. Chem., 10 (1973), 899–907) to react 1,2-dimethyl-5-nitroimidazole with N,N-dimethylformamido-dicyclohexylacetal to give 2-(2-dimethylaminovinyl)-1-methyl-5-nitroimidazole (loc. cit., 899):

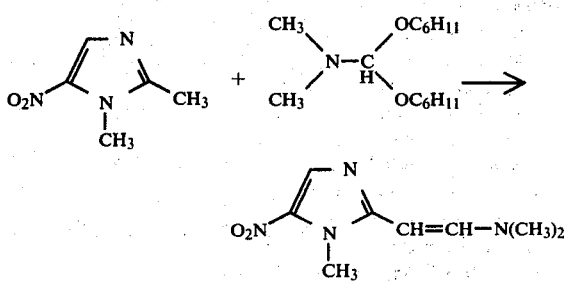

Oxidation of the side chain with oxygen in the presence of copper-(I) chloride or of photosensitizers proved unsuccessful (loc. cit., 900). Only on using more powerful oxidizing agents, eg. ozone or osmium tetroxide (Ann., loc. cit., 1,467, 1,468, 1,474) did it prove possible to prepare the aldehyde in better yields. However, larger amounts of 2-formyl-1-methyl-5-nitroimidazole cannot be prepared simply and economically by this method.

As disclosed in German laid open-application DOS No. 2,521,046 (page 15 and 16), 1,2-dimethyl-5-nitroimidazole can be reacted with benzaldehyde in the presence of a base, eg. sodium ethoxide in absolute ethanol, to give 1-methyl-5-nitro-2-styrylimidazole and the latter can be oxidized with ozone or alkali metal periodate and osmium tetroxide, in the course of from 10 to 20 hours, to give the aldehyde.

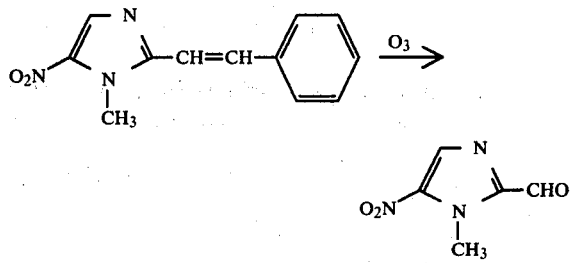

These processes are unsatisfactory in that they do not offer simple and economical operation and do not use readily available reactants.

The reaction of 1,2-dimethyl-5-nitroimidazole with oxalic acid ethyl ester chloride in the course of 22 hours in the presence of triethylamine and of substantial amounts of ether gives 1-carbethoxy-2-(1-methyl-5-nitro-imidazol-2-yl)-vinyl ethyl oxalate in 54 percent yield; the latter compound on treatment with ethanol, gives 1-methyl-5-nitroimidazol-2-yl-pyruvic acid ethyl ester in 43 percent yield (J. Heterocycl., loc. cit., 904 and 905).

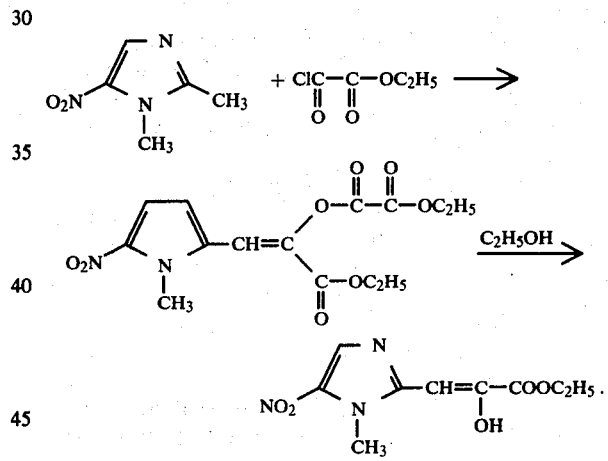

We have found that a 2-substituted 1-alkyl-nitroimidazole of the formula

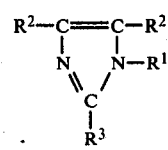

where $R^1$ is an aliphatic radical, one $R^2$ is nitro and the other $R^2$ is an aliphatic radical or hydrogen, $R^3$ is

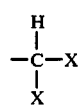

or —CHO and X is halogen, is obtained in an advantageous manner by a process wherein, in a first stage, a 2-methylnitroimidazole of the formula

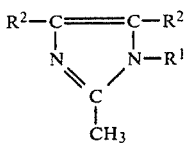

where R¹ and R² have the above meanings, is reacted with an oxalic acid diester of the formula

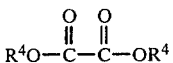

where the individual radicals R⁴ may be identical or different and each is an aliphatic, cycloaliphatic or araliphatic radical, in the presence of a basic compound and of an organic solvent which is inert under the reaction conditions, and the resulting nitroimidazol-2-yl-pyruvic acid ester of the formula

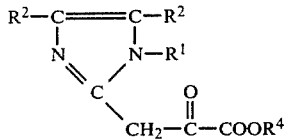

where R¹, R² and R⁴ have the above meanings, or its enolate, is reacted, in a second stage, with halogen in the presence of an acid, and, if desired, the resulting 2-dihalomethylnitroimidazole of the formula

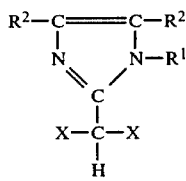

where R¹, R² and X have the above meanings, is reacted, in a third stage, with water in the presence of an acid to give a 2-formyl-nitroimidazole of the formula

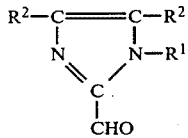

where R¹ and R² have the above meanings.

Further, we have found the novel 2-substituted 1-alkyl-nitroimidazoles of the formula

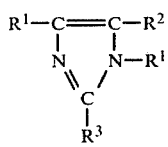

where R¹ is an aliphatic radical, one R² is nitro and the other R² is an aliphatic radical or hydrogen, R³ is

and X is halogen, and R³ can also be —CHO if R² in the 4-position of the molecule is nitro. Preferred compounds are 2-dichloromethyl-1-methyl-5-nitroimidazole, 2-dichloromethyl-1-methyl-4-nitroimidazole and 2-formyl-1-methyl-4-nitroimidazole.

Where 1,2-dimethyl-5-nitroimidazole, diethyl oxalate and chlorine are used, the reaction can be represented by the following equations:

Compared to the conventional processes, the process of the invention gives the novel 2-dihalomethyl-4-nitroimidazoles, 2-dihalomethyl-5-nitroimidazoles, the novel 2-formyl-4-nitroimidazoles and, more simply and more economically, the previously described 2-formyl-5-nitroimidazoles, in better yield and higher purity.

Oxalic acid diesters are industrially readily obtainable starting compounds. The novel process avoids the use of expensive oxidizing agents, such as manganese dioxide, noble metal oxides or ozone. The second stage (halogenation) and the third stage (hydrolysis) can also advantageously be carried out in the same vessel. The oxalic acid monoester simultaneously formed, or the oxalic acid liberated, can be isolated and re-used for the preparation of oxalic acid diesters. The aldehyde I formed on hydrolysis can, without isolation, be used for further syntheses, for example for converting salts of hydroxylamine, semicarbazide or thiosemicarbazide to the corresponding oxime, semicarbazone or thiosemicarbazone. All these advantageous results of the process according to the invention are surprising, since it would have been expected, from the prior art, that the halogenation could not be carried out, that the reaction with oxalic acid diesters would, at the very least, have given far lower yields and a far lower purity of compound IV, and that, overall, the process would not have been capable of being carried out on an industrial scale.

Starting material II can be reacted with starting material III in the stoichiometric amount or in excess, preferably in a ratio of from 1 to 3 moles of the latter per mole of the former. Preferred starting materials II and III and, accordingly, preferred compounds IV, V and VI and end products I are those where $R^1$ is alkyl of 1 to 7 carbon atoms, one $R^2$ is nitro and the other $R^2$ is alkyl of 1 to 7 carbon atoms or hydrogen, $R^3$ is

or —CHO, the individual radicals $R^4$ are identical or different and each is alkyl of 1 to 7 carbon atoms, cycloalkyl of 5 to 6 carbon atoms or aralkyl of 7 to 12 carbon atoms and X is bromine, iodine or especially chlorine. The above radicals can in addition be substituted by groups which are inert under the reaction conditions, for example alkyl of 1 to 4 carbon atoms, or nitro.

The following 2-methyl-nitroimidazoles are examples of suitable starting materials II: 4-nitro-, 5-nitro-, 4-nitro-5-methyl-, 4-nitro-5-ethyl-, 4-nitro-5-propyl-, 4-nitro-5-isopropyl-, 4-nitro-5-butyl-, 4-nitro-5-isobutyl-, 4-nitro-5-sec.-butyl-, 4-nitro-5-tert.-butyl-, 5-nitro-4-methyl-, 5-nitro-4-ethyl-, 5-nitro-4-propyl-, 5-nitro-4-isopropyl-, 5-nitro-4-butyl-, 5-nitro-4-isobutyl-, 5-nitro-4-sec.-butyl- and 5-nitro-4-tert.-butyl-1,2-dimethylimidazole, and corresponding 1-ethyl-, 1-propyl-, 1-isopropyl-, 1-butyl-, 1-isobutyl-, 1-sec.-butyl and 1-tert.-butyl-2-methyl-imidazoles which are unsubstituted in the 5-position or 4-position or are substituted in the above manner in the 4- and 5-positions.

The following oxalic acid diesters are examples of suitable starting materials III: dimethyl, diethyl, dipropyl, diisopropyl, dibutyl, diisobutyl, di-sec.-butyl, di-tert.-butyl, dicyclopentyl, dicyclohexyl, dibenzyl and diphenylethyl oxalate and monomethyl monoethyl oxalate.

The reaction in the first stage is carried out in the presence of a basic compound, advantageously using from 0.5 to 5, preferably from 1 to 3, equivalents of the latter per mole of starting material II. Suitable basic compounds are tertiary amines, alkaline earth metal compounds, ammonium compounds, tertiary phosphines and in particular alkali metal compounds, as well as mixtures of the above. Alcoholates, especially alkali metal alcoholates, are preferred, and amongst the alcoholates the alkanolates are particularly advantageous. Specific examples of suitable basic compounds are potassium hydroxide, sodium hydroxide, lithium hydroxide, calcium hydroxide, calcium oxide, barium oxide, magnesium hydroxide, magnesium oxide, barium hydroxide, magnesium acetate, sodium formate, sodium acetate, sodium propionate, sodium butyrate, sodium isobutyrate, potassium formate, potassium acetate, potassium propionate, potassium butyrate, potassium isobutyrate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N,N-dimethylaminoethanol, N,N-diethylaminoethanol, N,N-dipropylaminoethanol, N-methylpyrrolidone, N-ethylpyrrolidone, N-methylpiperidine, N-ethylpiperidine, N-methylpyrrolidine, N-ethylpyrrolidine, N-methylimidazole, N-ethylimidizaole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine, and as preferred compounds, sodium methylate, sodium ethylate, sodium propylate, sodium isopropylate, sodium butylate, sodium isobutylate, sodium sec.-butylate, sodium tert.-butylate, sodium ethylene-glycolate, sodium 1,2-propyleneglycolate, sodium 1,3-propylene-glycolate, sodium diethyleneglycolate, sodium triethyleneglycolate, sodium 1,2-dipropylene-glycolate, potassium methylate, potassium ethylate, potassium n-propylate, potassium isopropylate, potassium n-butylate, potassium isobutylate, potassium sec.-butylate, potassium tert.-butylate, potassium ethylene-glycolate, potassium 1,2-propylene-glycolate, potassium 1,3-propyleneglycolate, potassium diethylene-glycolate, potassium triethylene-glycolate and potassium 1,2-dipropylene-glycolate; those of the above alkanolates which are of 1 to 4 carbon atoms are particularly preferred.

The reaction in the first stage is in general carried out at from 0° to 120° C., preferably from 20° to 100° C., especially from 50° to 90° C., under atmospheric or, advantageously, superatmospheric pressure, continuously or batchwise. Solvents which are inert under the reaction conditions are used. Examples of suitable solvents are aromatic hydrocarbons, eg. toluene, ethylbenzene, o-, m- and p-xylene, isopropylbenzene and methylnapthalene, alkanols and cycloalkanols, eg. ethanol, methanol, n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol, methylcyclohexanol and diacetone-alcohol, especially those of 1 to 4 carbon atoms, and mixtures of the above. The solvent is advantageously used in an amount of from 100 to 10,000 percent by weight, preferably from 200 to 1,500 percent by weight, based on starting material II.

The first stage of the reaction can be carried out as follows: a mixture of starting material II and III together with the basic compound and the solvent is kept for from 0.5 to 24 hours at the reaction temperature. The starting material III or the starting material II can be mixed with a solvent, after which the other components are added. Compound IV is isolated from the reaction mixture in the conventional manner, advantageously by filtering, treating the filter residue with acid, eg. aqueous hydrochloric acid or sulfuric acid, and again filtering.

If enolate-forming basic compounds, for example metal alcoholates, eg. an alkali metal alkanolate, are used, the enolates of the compounds IV can be isolated in the filter residue during the first filtration. The enolates of the compounds IV are compounds of the formula

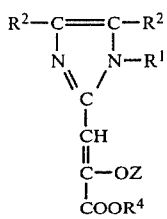

$$\begin{array}{c} R^2-C=\!\!=\!\!C-R^2 \\ | \quad\quad | \\ N \quad\quad N-R^1 \\ \backslash\!\!\diagup \\ C \\ | \\ CH \\ \| \\ C-OZ \\ | \\ COOR^4 \end{array} \quad\quad VII$$

where $R^1$, $R^2$ and $R^4$ have the above general or preferred meanings and Z is one equivalent of a metal atom, preferably of an alkali metal atom. Potassium enolates and especially sodium enolates VII are preferred. These enolates VII can also be reacted instead of the compounds IV in the second stage of the reaction.

In the second stage of the process according to the invention, compound IV or compound VII is reacted with halogen, preferably bromine, iodine and especially chlorine, in the stoichiometric amount or in excess, preferably in a ratio of from 2 to 2.5 moles of halogen, in particular $Cl_2$, per mole of starting material II. In this second stage of the process, the reaction is carried out in an acid medium, since hydrogen halide is formed. Preferably, an added acid is also used, advantageously in an amount of from 1 to 4, especially from 2 to 2.5, equivalents or, when using enolates VII, in an amount of from 2 to 5, especially from 3 to 3.5, equivalents per mole of starting material II. Inorganic or organic acids can be used. Instead of monobasic acids, equivalent amounts of polybasic acids can also be employed. Examples of suitable acids are the following: hydrogen chloride, hydrogen bromide, hydrogen iodide, perchloric acid, sulfuric acid, phosphoric acid, nitric acid, sulfonic acids, eg. benzenesulfonic acid and p-toluenesulfonic acid; boron-containing acids, eg. boric acid; aliphatic carboxylic acids, eg. chloroacetic acid, dichloroacetic acid, trichloroacetic acid, oxalic acid, formic acid, cyanoacetic acid, acetic acid, propionic acid, butyric acid, isobutyric acid, tartaric acid, citric acid, $\beta$-hydroxybutyric acid, caprylic acid, trimethylacetic acid, $\alpha$- and $\beta$-chloropropionic acid, succinic acid, isovaleric acid, valeric acid, glutaric acid, adipic acid and corresponding mixtures. The acids may be used in a concentrated form, as mixtures with one another and/or as mixtures with a solvent, especially water. In the case of dilute aqueous acids it is advantageous to use acids of from 15 to 35 percent strength by weight, for example hydrochloric acid of from 20 to 30 percent strength by weight, sulfuric acid of from 10 to 50, preferably from 20 to 30, percent strength by weight or acetic acid of from 50 to below 100 percent strength by weight. Hydrochloric acid, sulfuric acid, phosphoric acid, formic acid, acetic acid, monochloroacetic acid, dichloroacetic acid and trichloroacetic acid are preferred. The treatment pH is from 0 to 7, preferably from 1 to 6, especially from 2 to 3.

The reaction in the second stage is in general carried out at from $-5°$ to $+70°$ C., preferably from $0°$ to $50°$ C., especially from $10°$ to $25°$ C., under reduced, superatmospheric or atmospheric pressure, batchwise or continuously. Solvents which are inert under the reaction conditions are used. Examples of suitable solvents are those mentioned for the reaction of the first process stage, preferably water, and corresponding mixtures of solvents or mixtures of these solvents with water or the mixtures mentioned for the first process stage. The solvent is advantageously used in an amount of from 100 to 10,000 percent by weight, preferably from 200 to 1,500 percent by weight, based on starting material II.

The reaction can be carried out as follows: a mixture of starting material IV or VII, halogen, solvent and additional acid is kept at the reaction temperature for from 1 to 24 hours. Compound V is then isolated from the mixture in the conventional manner, for example by filtering, diluting the filtrate with ice water, neutralizing it with, for example, an alkali metal hydroxide solution and again filtering.

If desired, stages 1 and 2 of the process according to the invention can also be carried out as a one-vessel reaction, for example by carrying out the reaction in stage 1 in the manner described above, then adding to the reaction mixture additional acid, solvent, for example water, and halogen, in accordance with the process conditions for stage 2 described above, and thereafter carrying out the reaction of stage 2.

The second stage can also advantageously be followed by the third process stage. The starting material V is reacted with water in the stoichiometric amount or in excess, preferably with from 150 to 1,500, especially from 250 to 800, percent by weight of water, based on starting material V. Advantageously, all or part of the water is added in the form of a dilute acid. Since hydrogen halide is liberated in this stage also, the reaction takes place in an acid medium. As a rule, an added acid is used, advantageously in an amount of from 0.5 to 1.5 equivalents per mole of compound V. Inorganic or organic acids may be used, and instead of monobasic acids equivalent amounts of polybasic acids may be employed. Examples of suitable acids are the acids mentioned above as being suitable for stage 2 of the process according to the invention. The acids can be used in a concentrated form, as mixtures with one another and/or as mixtures with a solvent, especially water. In the case of dilute aqueous acids it is advantageous to use acids of from 3 to 30 percent strength by weight, for example hydrochloric acid of from 5 to 15 percent strength by weight, sulfuric acid of from 3 to 15, preferably from 5 to 15, percent strength by weight or phosphoric acid of from 5 to 20 percent strength by weight. Hydrochloric acid and sulfuric acid are preferred.

The reaction in the third stage is in general carried out at from $25°$ to $150°$ C., preferably from $80°$ to $110°$ C., under atmospheric or superatmospheric pressure, continuously or batchwise. With water present, it is not necessary additionally to use organic solvents which are inert under the reaction conditions, but the solvents already mentioned for the first and second process stage can, if desired, be present in the stated amounts.

The reaction can be carried out as follows: a mixture of starting material V, water and acid is kept at the reaction temperature for from 0.5 to 3 hours. The end product is then isolated from the reaction mixture in the conventional manner, for example by neutralizing, extracting with a suitable solvent, eg. methylene chloride, and distilling the extract.

The second and third stage can also be carried out as a one-vessel reaction, for example by carrying out the reaction of stage 2 in the manner described above, adding water and, if desired, additional acid to the reaction mixture in accordance with the above process conditions of stage 3, and carrying out the reaction of stage 3.

The novel and known end products I and compounds V and VI obtainable by the process of the invention are valuable starting materials for the preparation of dyes, pesticides and drugs. For example, they can be converted, by reaction with 3-amino-5-diethylaminomethyl-oxazolid-2-one, to (1-alkyl-5-nitroimidazol-2-yl)-N-(5-diethylaminomethyloxazolidin-2-on-3-yl)-azomethines which are drugs selectively active against trichomonads. With regard to the use of the compounds, reference may be made to the publications mentioned.

In the Examples which follow, parts are by weight and bear the same relation to parts by volume as that of the kilogram to the liter.

EXAMPLE 1

(a) Ethyl 1-methyl-5-nitroimidazol-2-yl-pyruvate

A mixture of 180 parts of a 30 percent strength by weight sodium methylate solution in methanol, 146 parts of diethyl oxalate and 150 parts by volume of ethanol is added in the course of 30 minutes, at 60° C., to a suspension of 141 parts of 1,2-dimethyl-5-nitroimidazole in 250 parts by volume of ethanol. After stirring for one hour at 60° C., the mixture is cooled and the sodium enolate of ethyl 1-methyl-5-nitroimidazol-2-yl-pyruvate is filtered off. The salt is then introduced into 1,300 parts by volume of 3 percent strength by weight hydrochloric acid, whilst stirring. The mixture is stirred for a further half-hour and the product is then filtered off. 190 parts (79% of theory) of ethyl 1-methyl-5-nitroimidazol-2-yl-pyruvate of melting point 141° C. (after recrystallization from ethanol) are obtained.

(b) 2-Dichloromethyl-1-methyl-5-nitroimidazole 142 parts of chlorine are passed into a suspension of 241 parts of ethyl 1-methyl-5-nitroimidazol-2-yl-pyruvate in 400 parts of water at 20° C. At the same time, 400 parts by volume of 50 percent strength by weight sulfuric acid are added in the course of 30 minutes. After completion of the reaction (which requires a total of 1.5 hours) the mixture is cooled and the oxalic acid which has precipitated is filtered off. The clear solution is then poured into ice water and the mixture is neutralized with 20 percent strength by weight aqueous sodium hydroxide solution, whilst cooling. The end product which has precipitated is filtered off and dried. 157 parts (75% of theory) of melting point 52° C. are obtained.

(c) 2-Formyl-1-methyl-5-nitroimidazole 210 parts of 2-dichloromethyl-1-methyl-5-nitroimidazole are stirred in 800 parts by volume of 10 percent strength by weight sulfuric acid for 2 hours at 100° C. The mixture is then neutralized with 550 parts of 6 N sodium hydroxide solution, with intense cooling, and the resulting solution is extracted with 4 times 500 parts by volume of methylene chloride. The combined extracts are dried. 126 parts (82% of theory) of 2-formyl-1-methyl-5-nitroimidazole of melting point 93° C. (after recrystallization from toluene) are obtained.

EXAMPLE 2

(a) Methyl 1-methyl-4-nitroimidazol-2-yl-pyruvate

A mixture of 73 parts of diethyl oxalate, 250 parts by volume of toluene and 90 parts of a 30 percent strength by weight sodium methylate solution in methanol is added to a suspension, at 80° C., of 70.5 parts of 1,2-dimethyl-4-nitroimidazole in 350 parts by volume of toluene. After stirring for two hours at 80° C., the mixture is cooled and the product is filtered off. The filter residue is treated with methylene chloride and the sodium enolate formed is suspended in water. This mixture is neutralized with 100 parts of 18 percent strength by weight hydrochloric acid. The methyl 1-methyl-4-nitroimidazol-2-yl-pyruvate which has precipitated is filtered off, dried and taken up in methylene chloride. The insoluble constituent is then filtered off and the filtrate is concentrated to dryness under reduced pressure. 45 parts of methyl 1-methyl-4-nitroimidazol-2-yl-pyruvate (40% of theory) of melting point 186° C. are obtained.

(b) 2-Dichloromethyl-1-methyl-4-nitroimidazole 8 parts of chlorine are passed into a solution of 11.3 parts of methyl 1-methyl-4-nitroimidazol-2-yl-pyruvate in 75 parts by volume of 30 percent strength by weight sulfuric acid at 20° C. in the course of 30 minutes. The solution is then poured onto ice and neutralized with 90 parts of 20 percent strength by weight sodium hydroxide solution, whilst cooling. The 2-dichloromethyl-1-methyl-4-nitroimidazole which precipitates is filtered off. 5 parts (47% of theory) of 2-dichloromethyl-1-methyl-4-nitroimidazole of melting point 153° C. are obtained.

(c) 2-Formyl-1-methyl-4-nitroimidazole 21 parts of 2-dichloromethyl-1-methyl-4-nitroimidazole in 80 parts by volume of 10 percent strength by weight sulfuric acid are stirred for 2 hours at 100° C. The solution is cooled, poured onto ice and neutralized with 55 parts of 6 N sodium hydroxide solution. The aqueous phase is extracted with 4 times 50 parts by volume of methylene chloride. The combined extracts are dried and evaporated. 13 parts of 2-formyl-1-methyl-4-nitroimidazole (83% of theory) of melting point 129° C. are obtained.

We claim:

1. A process for the preparation of a 2-substituted 1-alkyl-nitroimidazole of the formula

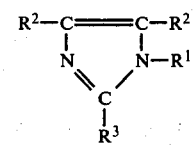

I where $R^1$ is an aliphatic radical, one $R^2$ is nitro and the other $R^2$ is an aliphatic radical or hydrogen, $R^3$ is

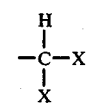

or —CHO and X is halogen, wherein, in a first stage, a 2-methylnitroimidazole of the formula

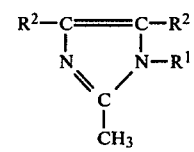

II where $R^1$ and $R^2$ have the above meanings, is reacted with an oxalic acid diester of the formula

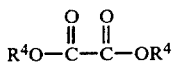

where the individual radicals $R^4$ may be identical or different and each is an aliphatic, cycloaliphatic or araliphatic radical, in the presence of a basic compound and of an organic solvent which is inert under the reaction conditions, and the resulting nitroimidazol-2-yl-pyruvic acid ester of the formula

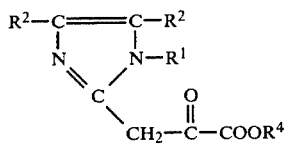

where $R^1$, $R^2$ and $R^4$ have the above meanings, or its enolate, is reacted, in a second stage with halogen in the presence of an acid, and, if desired, the resulting 2-dihalomethylnitroimidazole of the formula

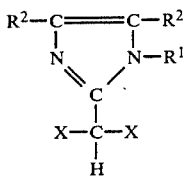

where $R^1$, $R^2$ and X have the above meanings, is reacted, in a third stage, with water in the presence of an acid to give a 2-formyl-nitroimidazole of the formula

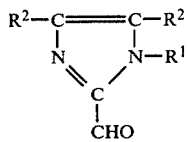

where $R^1$ and $R^2$ have the above meanings.

2. A process as claimed in claim 1, wherein the reaction is carried out with a ratio of from 1 to 3 moles of starting material III per mole of starting material II.

3. A process as claimed in claim 1, wherein the reaction in the first stage is carried out with from 0.5 to 5 equivalents of a basic compound per mole of starting material II.

4. A process as claimed in claim 1, wherein the reaction in the first stage is carried out with a tertiary amine, alkaline earth metal compound, ammonium compound, tertiary phosphine, alkali metal compound or mixture of these as the basic compound.

5. A process as claimed in claim 1, wherein the reaction in the first stage is carried out at from 0° to 120° C.

6. A process as claimed in claim 1, wherein the reaction is carried out using a solvent which is inert under the reaction conditions.

7. A process as claimed in claim 1, wherein the reaction is carried out using a solvent in an amount of from 100 to 10,000 percent by weight, based on starting material II.

8. A process as claimed in claim 1, wherein the reaction in the second stage is carried out with a ratio of from 2 to 2.5 moles of halogen per mole of starting material IV.

9. A process as claimed in claim 1, wherein the reaction in the second stage is carried out with from 1 to 4 equivalents of acid per mole of starting material IV.

10. A process as claimed in claim 1, wherein the reaction in the second stage, when using an enolate IV, is carried out with from 2 to 5 equivalents of acid per mole of starting material IV.

11. A process as claimed in claim 1, wherein the reaction in the second stage is carried out at from −5° to +70° C.

12. A process as claimed in claim 1, wherein the reaction is carried out as a one-vessel process by carrying out the reaction of stage 1 in the above manner, adding additional acid, solvent, water and halogen to the reaction mixture for stage 2 and then carrying out the reaction of stage 2.

13. A process as claimed in claim 1, wherein the reaction in the third process stage is carried out with from 150 to 1,500 percent by weight of water, based on starting material V.

14. A process as claimed in claim 1, wherein the reaction in the third process stage is carried out with from 0.5 to 1.5 equivalents of acid per mole of material V.

15. A process as claimed in claim 1, wherein the reaction in the third process stage is carried out at from 25° to 150° C.

16. A process as claimed in claim 1, wherein the reaction in all three stages is carried out as a one-vessel reaction.

* * * * *